(12) United States Patent
Drexler

(10) Patent No.: US 11,174,161 B2
(45) Date of Patent: Nov. 16, 2021

(54) MOLECULAR MOTOR

(71) Applicant: Kim Eric Drexler, Oxford (GB)

(72) Inventor: Kim Eric Drexler, Oxford (GB)

(73) Assignee: Kim Eric Dexler, Oxford (GB)

( * ) Notice: Subject to any disclaimer, the term of this patent is extended or adjusted under 35 U.S.C. 154(b) by 1099 days.

(21) Appl. No.: 15/551,445

(22) PCT Filed: Feb. 16, 2016

(86) PCT No.: PCT/GB2016/050380
§ 371 (c)(1),
(2) Date: Aug. 16, 2017

(87) PCT Pub. No.: WO2016/132114
PCT Pub. Date: Aug. 25, 2016

(65) Prior Publication Data
US 2018/0037456 A1   Feb. 8, 2018

(30) Foreign Application Priority Data

Feb. 20, 2015   (GB) ..................... 1502866

(51) Int. Cl.
*B82B 1/00* (2006.01)
*H02N 11/00* (2006.01)
*B82Y 5/00* (2011.01)

(52) U.S. Cl.
CPC ........... *B82B 1/003* (2013.01); *H02N 11/006* (2013.01); *B82Y 5/00* (2013.01)

(58) Field of Classification Search
CPC ........... B82B 1/00; B82B 1/003; B82B 1/006; B82B 1/008; B82Y 15/00; H02N 11/00; H02N 11/006
See application file for complete search history.

(56) References Cited

U.S. PATENT DOCUMENTS

| | | | |
|---|---|---|---|
| 2010/0016608 A1* | 1/2010 | Irie | B81B 3/0029 548/202 |
| 2010/0076180 A1* | 3/2010 | Fujita | H02N 11/006 530/402 |
| 2012/0175529 A1* | 7/2012 | Naciri | C08F 220/36 250/492.1 |
| 2014/0234948 A1 | 8/2014 | Schneider et al. | |

FOREIGN PATENT DOCUMENTS

WO   WO 00/22101 A2   4/2000

OTHER PUBLICATIONS

Balzani, "Photochemical molecular devices," *Photochem. Photobiol. Sci.*, 2003, 2, pp. 459-476.

Diring et al., "Star-Shaped Multichromophoric Arrays from Bodipy Dyes Grafted on Truxene Core," *J. Am. Chem. Soc.*, 2009, 131(17), pp. 6108-6110.

(Continued)

*Primary Examiner* — Quyen P Leung
*Assistant Examiner* — Minki Chang
(74) *Attorney, Agent, or Firm* — Leydig, Voit & Mayer, Ltd.

(57) ABSTRACT

There is disclosed a microscale or nanoscale stepper motor in which one or more arrays of corresponding types of optically switchable molecular actuators are used to drive progressive motion between bodies of the motor.

42 Claims, 7 Drawing Sheets

(56) References Cited

OTHER PUBLICATIONS

Grigoryan et al., "Computational design of virus-like protein assemblies on carbon nanotube surfaces," *Science*, May 27, 2011, 332, pp. 1071-1076.

Ilk et al., "S-layer fusion proteins—construction principles and applications", Current Opinion in Biotechnology, Dec. 2011, 22(6), pp. 824-831.

Ilk et al., "Surfaces functionalized with self-assembling S-layer fusion proteins for nanobiotechnological applications," *Colloids and Surfaces A: Physiochemical and Engineering Aspects*, May 15, 2008, 321(1-3), pp. 163-167, Organised Molecular Films Selected papers from LB12—the 12th International Conference on Organized Molecular Films, Jul. 1-5, 2007, Krakow, Poland.

Lopes et al., "Computational design of protein-ligand binding: Modifying the specificity of asparaginyl-tRNA synthetase," *J. of Computational Chemistry*, Apr. 30, 2010, 31(6), pp. 1273-1286.

McMillan et al., "A Self-Assembling Protein Template for Constrained Synthesis and Patterning of Nanoparticle Arrays," *J. Am. Chem. Soc.*, 2005, 127(9), pp. 2800-2801.

Miller et al., "Self-assembling light-harvesting systems from synthetically modified tobacco mosaic virus coat proteins," *J. Am. Chem. Soc.*, 2007, 129(11), pp. 3104-3109.

Skerra, "Alternative binding proteins: Anticalins—harnessing the structural plasticity of the lipocalin ligand pocket to engineer novel binding activities," *FEBS Journal*, Jun. 2008, 275(11), pp. 2677-2683.

Sleytr et al., "Nanobiotechnology with S-layer proteins as building blocks," *Progress in Molecular Biology and Translational Science*, 2011, 103, pp. 277-352.

Sleytr et al., "S-Layers as a basic building block in a molecular construction kit," *FEBS Journal*, Jan. 2007, 274(2), pp. 323-334.

Tang et al., "Recognition Imaging and Highly Ordered Molecular Templating of Bacterial S-Layer Nanoarrays Containing Affinity-Tags," *Nano Lett.*, 2008, 8(12), pp. 4312-4319.

Tinberg et al., "Computational design of ligand-binding proteins with high affinity and selectivity," *Nature*, Sep. 12, 2013, 501, pp. 212-216.

Wang, "Optimally controlled optomechanical work cycle for a molecular locomotive," *J. Phys. Condens. Matter*, 2005, 17, pp. S3767-S3782.

Yamada et al., "Photomobile polymer materials—various three-dimensional movements," *J. of Materials Chemistry*, Jan. 1, 2009, 19(1), pp. 60-62.

Yilmaz et al., "Light harvesting and efficient energy transfer in a boron-dipyrrin (BODIPY) functionalized perylenediimide derivative," *Org. Lett.*, 2006, 8(13), pp. 2871-2873.

Yuan et al., "Light Harvesting and Efficient Energy Transfer in Dendritic Systems: New Strategy for Functionalized Near-Infrared BF2-Azadipyrromethenes," *Chemistry—An Asian Journal*, May 4, 2009, 4(5), pp. 707-713.

European Patent Office, International Search Report in International Patent Application No. PCT/GB2016/050380, dated May 6, 2016, 2 pp.

European Patent Office, Written Opinion in International Patent Application No. PCT/GB2016/050380, dated May 6, 2016, 6 pp.

United Kingdom Intellectual Property Office, Search Report in United Kingdom Patent Application No. GB1502866.5, dated Sep. 28, 2015, 1 p.

United Kingdom Intellectual Property Office, Search Report in United Kingdom Patent Application No. GB1602721.1, dated Sep. 19, 2015, 4 pp.

\* cited by examiner

MOLECULAR MOTOR

CROSS-REFERENCE TO RELATED APPLICATIONS

This application is a national phase application of International Patent Application No. PCT/GB2016/050380, filed Feb. 16, 2016, which claims priority to Great Britain Patent Application No. 1502866.5, filed Feb. 20, 2015, both of which are incorporated by reference herein in their entireties for all purposes.

FIELD OF THE INVENTION

The present invention relates to a motor, for example a molecular microscale or nanoscale motor in which molecules or moieties are used to drive a progressive motor action between opposing bodies of the motor.

INTRODUCTION

Very small synthetic motors constructed so as to provide a motor action through molecular activity have been proposed, for example in US2014/0234948, in which concentric cylinder surfaces are coated with complementary motor protein pairs such as actin and myosin. Applications for the motor suggested in this prior art publication include the replacement of neuromuscular function, or to perform the mechanical functions of a prosthetic implant.

It would be desirable to address the limitations of the related prior art.

SUMMARY OF THE INVENTION

The invention provides methods and apparatus which use pulsed optical signals to drive controlled, stepwise, and preferably reversible motions in microscale and nanoscale devices. Such a device may be described as a motor, for example as a nanoscale stepper motor. By suitable arrangement and design, such motors can be constructed so as to step under the application of different combinations and sequences of optical pulses, enabling independent control of distinct motions, for example sequences of stepwise displacements along one or more axes. Such devices and combinations of devices may be used, for example, to provide a 1, 2 or 3-dimensional positioning device or mechanism for a variety of purposes.

Prior art molecular motors employing actin and myosin cannot be controlled by external signals to drive timed sequences of discrete steps. That is, they cannot serve as stepper motors. Stepper motors are critical components of many devices, including 3D printers, but macroscale motors are not suitable for nanoscale positioning. Controlled, nanoscale stepper motors have potential applications in devices analogous to 3D printing systems that differ from prior art systems in that they can place well-defined nanoscale building blocks to build larger structures, rather than placing amounts of material in the much larger micron to millimetre range.

Typically, such motors may operate by each step comprising transitions through or between multiple adjacent alignments between two bodies of the motor, for example using two, three or more such alignments in series for each step. A first such alignment may occur in the absence of substantial optical activation, and at least a second such alignment then may be induced by a first optical driving signal or type of optical activation. A third such alignment may then be induced by a second optical driving signal or type of optical activation, following which the first alignment is again induced (but now displaced by a step) by a further absence of substantial optical activation. Alternatively, further alignments may be induced by corresponding driving signals, or the second alignment could be a transient alignment as the two bodies move from the second back to the first alignment (again, now displaced by a step), for example under particular forces or thermal motion.

Preferably, at least three alignments are provided in each step, in order to provide for reversible motion. In motors where only two alignments are provided in each step, means for altering the interaction profile between the bodies may be provided in order to provide steps of the motor in both forward and reverse directions, and/or to provide a non-stepwise reverse motion (for example to "reset" the motor or device).

The different optical driving signals or optical activation may comprise pulses of light that differ in various combinations of wavelength, intensity, and/or duration.

Such a motor, using large numbers of molecular actuators to control or drive the motion, may be configured to work reliably despite the occurrence of substantial incidence of mis-activation, misplacement, failure or omission of a significant fraction of the molecular actuators. Failed molecular actuators could be replaced by exchange and binding of fresh molecular components from a solution within which the motor is disposed or operating.

The invention therefore provides use of one or more different molecules, each of which is switchable between at least two different states of that molecule by a corresponding control signal, as molecular actuators in a nanoscale stepper motor. Each of the one or more different molecules may be switchable between the at least two different states using a mechanism or control signal which is physical, rather than chemical. The mechanism or control signal may therefore act remotely on, or externally from, the stepper motor. For example an optical mechanism or control signal using electromagnetic radiation, such as a beam of light, provided or generated externally to the stepper motor may be used, or other remote or external signals such as electric or magnetic fields may be used.

In order to provide a suitable stepper motor action, the different molecules may be switchable between their states reversibly, in both directions, or cyclically, so that a desired switching action or sequence can be repeated under control of the control signals.

The invention also provides a method comprising: disposing one or more distributions or arrays of such molecular actuators, such as optically switchable molecular actuators, between opposing bodies; and supplying a sequence of such control signals, for example optical signals, for example a repeated sequence of such signals, which switch the molecular actuators so as to provide a progressive motor action between the bodies. The distributions of optically switchable molecular actuators may be disposed between the opposing bodies in a configuration such that each repeated sequence urges or induces the opposing bodies into two, or into at least three different alignments, each alignment corresponding to a different combination of none, one or more of said optical signals.

Corresponding methods of providing and/or operating a suitable molecular motor may also be provided.

The invention also provides a motor comprising: first and second bodies in confrontation with each other, and at least a first distribution of a corresponding first type of optically switchable molecular actuator, each distribution being fixed on or attached to one of the first and second bodies. For each type of molecular actuator, the molecular actuators of that type are arranged to be optically switchable together between at least two different molecular states so as to change their state of interaction with the other of the bodies. In this way, repeated optical switching of the at least a first distribution provides a motor action to drive progressive movement of the first and second bodies relative to each other. As mentioned above, other types of remote action or external action switching may be used, and the molecular actuators may be reversibly or cyclically switchable between the corresponding molecular states in order to provide the repeated optical switching required for a progressive movement. In particular, the motor may provide movement between at least two distinct alignments of the bodies as part of each step of motion, the currently induced alignment being dependent on the current state of optical switching i.e. of the optical driving signals.

More specifically, the motor may comprise at least two such distributions, each of a different corresponding type of optically switchable molecular actuator, each distribution being fixed on one of the first and second bodies, the molecular actuators of each type being optically switchable independently, or substantially independently from each other to the extent required to drive progressive movement of the first and second bodies relative to each other. This progressive movement then takes the form of steps in which each step comprises a series of transitions between three or more distinct alignments. Of course, when we refer to the actuators of each type being switchable independently or substantially independently, this will likely include some activation of actuators which were not intended to be activated, for example due to overlapping absorption bands, failed activation of individual actuators for a variety of reasons, and other causes. For example, actuation may involve switching at least 75% or more preferably at least 90% of the actuators intended to be switched by a particular optical signal, and switching less than 25% or more preferably less than 10% of the actuators not intended to be switched by a particular optical signal.

The distributions of molecular actuators are typically in the form of arrays distributed across the relevant surfaces of the bodies within the interface. A periodic or quasi-periodic nature of the distributions or arrays may be used in order to provide the alignments. A particular and repeated sequence of movements between the alignments then makes up each repeated step of motion of the motor. To this end, the distributions or arrays may be regular arrays. Such arrays may be one or two dimensional, and if two dimensional may take various forms such as rectilinear, hexagonal etc., and such distributions maybe interleaved with each other or separately arranged.

The motion driven by the motor may be linear, rotational, or a combination of the two, for example depending on the arrangement and configuration of the opposing bodies. The motion driven by a particular motor may also be along or about a single axis, or along or about multiple axes. Motors as described herein may also be coupled or combined together to provide multi-axis movement.

The molecular actuators may be provided by a range of molecules or moieties which provide a change of state or configuration, including providing a change in one or more physical and/or chemical properties, when switched. A reversal of the change of state or configuration may typically occur through thermal relaxation. Suitable molecules or moieties could for example include molecules in the classes of azobenzenes (including heterocyclic and naphtyl moieties), diarylethenes, stilbenes or fulgide molecules which can be switched by optical signals of different wavelength can be used. Molecular structures including these types of molecule may also be adapted to respond to particular optical signals for example by using light antennae to capture and transmit the energy of optical signals of different wavelength to that which would natively switch the molecule or moiety. Actuator response to particular optical signals could also or instead be blocked by mechanical/steric means.

The invention also provides apparatus comprising one or more light sources arranged to provide the driving signals to drive one or more of the motors, for example by selectively optically switching the molecular actuators of each type. Such optical sources may be integrated with one or more of said motors, and such apparatus may also comprise one or more controllers to provide suitable control signals to the optical sources.

The invention also provides a plurality of motors as set out herein, wherein each motor comprises a plurality of said types of optically switchable molecular actuators, each motor comprising at least one said type of molecular actuator in common with at least one other of the motors, each motor being drivable by a different combination of optical signals to each of the other molecular actuators.

The invention also provides an actuator comprising one or more of the motors described herein. Such an actuator may for example be a rotational actuator, a linear actuator, a multi-axis actuator and so forth.

The invention also provides methods corresponding to the described apparatus, for example methods of fabrication or construction, and methods of operation of the described apparatus in its various aspects.

The invention maybe used for a variety of purposes, for example to carry out small scale 3D printing, for activation and control within medical devices and in a variety of other fields such as microfluidics, optical computing, and lithographic patterning of surfaces.

Although the above discussion refers to optical activation and switching of the molecular actuators, the invention also applies where different mechanisms are used in addition or instead of optical actuation, for example switching or activation using thermal, magnetic, electrical, acoustic, chemical or other types of driving signals. Actuation and switching may also or instead be performed using electromagnetic radiation other than optical radiation such as millimetre and longer waves including microwave and radio waves, as well as other sorts. When we refer to optically switchable actuators we are referring to the use of electromagnetic radiation in the ultraviolet and infrared regions, as well as visible radiation.

In at least one embodiment, the invention includes a motor having first and second bodies in confrontation with each other, and at least a first array of a corresponding first type of optically switchable molecular actuator, each array being fixed on one of the first and second bodies, for each type of molecular actuator, the molecular actuators of that type being optically switchable together between at least two different molecular states so as to change their state of interaction with the other of the bodies, such that repeated optical switching of the at least a first array provides a motor action to drive progressive movement of the first and second bodies relative to each other. In at least one embodiment, the at least a first array further includes at least two arrays each of a different corresponding type of optically switchable molecular actuator, each array being fixed on one of the first and second bodies, the molecular actuators of each type being optically switchable substantially independently from each other to drive progressive movement of the first and second bodies relative to each other. In at least one embodiment, the repeated optical switching includes repeating an ordered switching of each of the types of optical switchable molecular actuator in a first order. In at least one embodiment, the motor is arranged such that repeating the ordered switching in the first order drives said progressive movement in a first direction, and repeating the ordered switching in one or more other orders different to the first order drives said progressive movement in one or more other directions different to said first direction. In at least one embodiment, the one or more other orders include a second order which is the reverse of the first order. In at least one embodiment, the one or more other directions includes a second direction which is the opposite of the first direction.

In at least one embodiment of the inventive motor, the first order includes at least three time intervals in each of which a different combination of none, one or more of the different types of molecular actuator are activated. In at least one embodiment, the first order includes at least one-time interval in which one of the types of molecular actuator is optically activated and the other is not optically activated.

In at least one embodiment of the inventive motor, at least two of the arrays are fixed on the same body as each other.

In at least one embodiment of the inventive motor, at least two of the arrays are interleaved with each other.

In at least one embodiment of the motor, one or more of the arrays are regular arrays.

In at least one embodiment of the invention, the motor is arranged such that the repeated optical switching of the first array drives said progressive movement in a first direction.

In at least one embodiment, the motor is arranged such that the other of the bodies is modifiable such that repeated optical switching of the first array drives said progressive movement in a second direction opposite to the first direction.

In at least one embodiment of the inventive motor, the states of interaction give rise to a series of stepper positions in the movement of the first and second bodies relative to each other, such that the progressive movement in a particular direction includes repeated movement to subsequent stepper positions in that direction. In at least one embodiment, the motor further includes one or more arrays of passive features each array being disposed on one of the bodies, each such array of passive features being arranged to engage with at least one of the arrays of optically switchable molecular actuators disposed on the other of the bodies to thereby define the series of stepper positions. In at least one embodiment of the invention, one or more of the arrays of passive features includes an array of passive molecular elements which are not optically switched when any of the molecular actuators are switched. In at least one embodiment of the invention, at least one of the arrays of molecular actuators is arranged to change its state of engagement with at least one of the arrays of passive features when the said array of molecular actuators is optically switched. In at least one embodiment of the invention, the motor includes one or more of: at least three arrays of molecular actuators of different types: and at least two arrays of molecular actuators of different types and one array of passive elements.

In at least one embodiment of the inventive motor, each molecular actuator of each of one or more of said different types of molecular actuator includes a molecule from the class of azobenzene molecules. In at least one embodiment, each different type of molecular actuator including a molecule from the class of azobenzene molecules includes a different type of azobenzene molecule or moiety.

In at least one embodiment of the inventive motor, each molecular actuator of each of one or more of said different types of molecular actuator includes or is coupled to one or more a light-harvesting molecules or moieties. In at least one embodiment, the light-harvesting molecules or one or more of said different types of molecular actuator includes a BODIPY molecule.

In at least one embodiment of the inventive motor, each of one or more of the different types of molecular actuator is switchable using a different spectrum of light.

In at least one embodiment of the inventive motor, each of one or more of the different types of molecular actuator is switchable using a different envelope over time of intensity of light.

In at least one embodiment of the inventive motor, being optically switchable between at least two different molecular states includes being optically switchable between at least two different molecular conformations.

In at least one embodiment of the inventive motor, being optically switchable between at least two different molecular states includes being optically switchable between at least two different states of charge distribution.

In at least one embodiment of the inventive motor, each molecular actuator of each of one or more of said different types of molecular actuator is in communication with at least two light harvesting molecules.

At least one embodiment of the inventive motor further includes one or more light sources arranged to selectively optically switch the molecular actuators of each type.

In at least one embodiment of the invention, the motor further includes a controller arranged to control the one or more light sources so as to drive progressive movement of the first and second bodies relative to each other.

In at least one embodiment, the invention includes a plurality of motors wherein each motor includes a plurality of said types of optically switchable molecular actuators, each motor including at least one said type of molecular actuator in common with at least one other of the motors, each motor being drivable by a different combination of optical signals to each of the other molecular actuators. In at least one embodiment, the plurality of motors is arranged such that they all receive the same optical signals as each other. In at least one embodiment, each of the plurality of motors is arranged to provide a motor action including progressive movement along a different axis to each of the other motors. In at least one embodiment, the plurality of motors is coupled to a common mechanical load.

In another aspect of the invention, there is provided a method including providing first and second bodies in confrontation with each other and at least a first array of a corresponding first type of optically switchable molecular actuator, each array being fixed on one of the first and second bodies; providing repeated switching of the at least a first array to provide progressive movement of the first and second bodies relative to each other. In at least one embodiment of the method, the at least a first array includes at least two arrays each of a different corresponding different type of optically switchable molecular actuator, each array being fixed on one of the first and second bodies, the method including independently switching the molecular actuators of each type to provide said progressive movement. In at least one embodiment of the method, independently switching the molecular actuators of each type to provide said progressive movement includes repeating an ordered switching of each of the types of optical switchable molecular actuator. At least one embodiment of the method includes reversing the order of the ordered switching to provide progressive movement in a reverse direction. In at least one embodiment of the method, the repeated switching order includes at least three time intervals in each of which a different combination of none, one, or more than one of the different types of molecular actuator are activated. In at least one embodiment of the method, one or more of the types of molecular actuators includes an azobenzene molecule or moiety. In at least one embodiment of the method, each molecular actuator is switchable using a different optical signal, the different optical signals including one or more of different frequency spectra: and different intensity profiles over time.

In yet another aspect of the invention, there is a provided a method including disposing one or more arrays of optically switchable molecular actuators between opposing bodies, and supplying a repeated sequence of optical signals which switch the molecular actuators so as to provide a progressive motor action between the bodies. In at least one embodiment of the method, the arrays of optically switchable molecular actuators are disposed between the opposing bodies in a configuration such that each repeated sequence urges the opposing bodies into at least three different alignments, each alignment corresponding to a different combination of none, one or more of said optical signals.

Yet another aspect of the invention provides the use of one or more different molecules, each of which is switchable between at least two different states by a corresponding control signal, as molecular actuators in a nanoscale stepper motor. In at least one embodiment of such a use, each of the one or more different molecules are optically switchable between at least two different states. In at least one embodiment of such a use, the molecules include one or more of: azobenzenes, aromatically linked pyridines, diarylethenes, dithienylethenes, stilbenes, spiropyrans, fulgides, and phenoxynaphthacene quinones. In at least one embodiment of such a use, one or more of the molecules are in communication with a light harvesting molecule coupling the corresponding control signal to the molecule.

BRIEF DESCRIPTION OF THE DRAWINGS

Embodiments of the invention will now be described, by way of example only, with reference to the drawings of which.

DETAILED DESCRIPTION OF EMBODIMENTS

Figure 1:
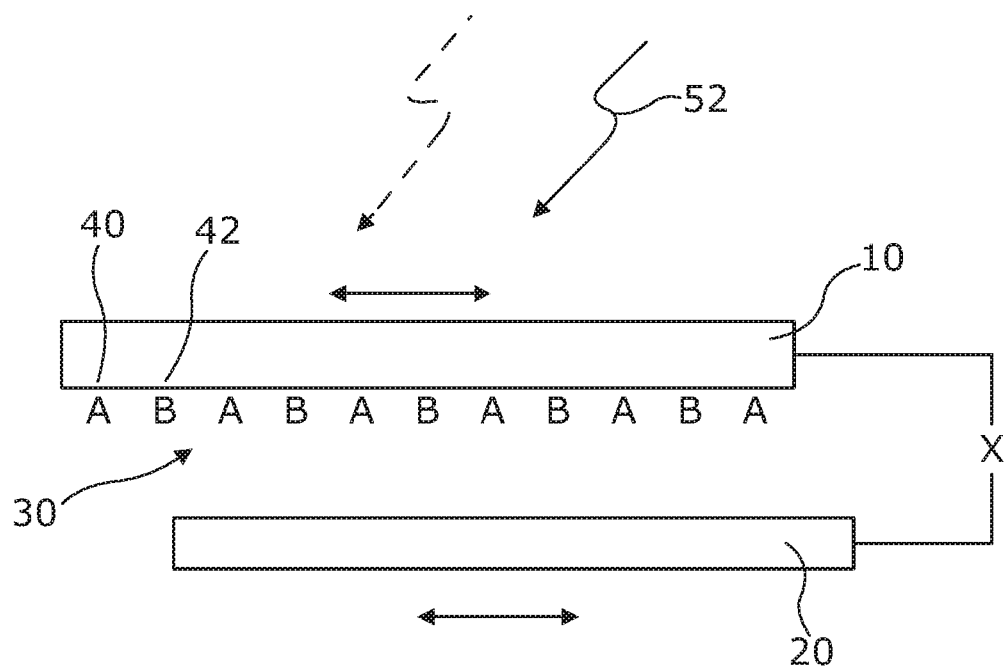
FIG. 1 illustrates a motor device according to the invention in which at least two types of molecular actuator (A and B) are provided in the interface between opposing motor bodies.

Referring now to FIG. 1, there is illustrated schematically a motor driven by optically switchable molecular actuators. Since each molecular actuator may be of the order of nanometers in size, and the motor action can therefore move in steps or a corresponding scale, the motor may be described as a nanoscale motor. In at least one embodiment, the invention includes a motor having first and second bodies in confrontation with each other, and at least a first array of a corresponding first type of optically switchable molecular actuator, each array being fixed on one of the first and second bodies, for each type of molecular actuator, the molecular actuators of that type being optically switchable together between at least two different molecular states so as to change their state of interaction with the other of the bodies, such that repeated optical switching of the at least a first array provides a motor action to drive progressive movement of the first and second bodies relative to each other. In at least one embodiment, the at least a first array further includes at least two arrays each of a different corresponding type of optically switchable molecular actuator, each array being fixed on one of the first and second bodies, the molecular actuators of each type being optically switchable substantially independently from each other to drive progressive movement of the first and second bodies relative to each other. In at least one embodiment, the repeated optical switching includes repeating an ordered switching of each of the types of optical switchable molecular actuator in a first order. In at least one embodiment, the motor is arranged such that repeating the ordered switching in the first order drives said progressive movement in a first direction, and repeating the ordered switching in one or more other orders different to the first order drives said progressive movement in one or more other directions different to said first direction. In at least one embodiment, the one or more other orders include a second order which is the reverse of the first order. In at least one embodiment, the one or more other directions includes a second direction which is the opposite of the first direction.

In at least one embodiment of the inventive motor, the first order includes at least three time intervals in each of which a different combination of none, one or more of the different types of molecular actuator are activated. In at least one embodiment, the first order includes at least one-time interval in which one of the types of molecular actuator is optically activated and the other is not optically activated.

In at least one embodiment of the inventive motor, at least two of the arrays are fixed on the same body as each other.

In at least one embodiment of the inventive motor, at least two of the arrays are interleaved with each other.

In at least one embodiment of the motor, one or more of the arrays are regular arrays.

In at least one embodiment of the invention, the motor is arranged such that the repeated optical switching of the first array drives said progressive movement in a first direction.

In at least one embodiment, the motor is arranged such that the other of the bodies is modifiable such that repeated optical switching of the first array drives said progressive movement in a second direction opposite to the first direction.

In at least one embodiment of the inventive motor, the states of interaction give rise to a series of stepper positions in the movement of the first and second bodies relative to each other, such that the progressive movement in a particular direction includes repeated movement to subsequent stepper positions in that direction. In at least one embodiment, the motor further includes one or more arrays of passive features each array being disposed on one of the bodies, each such array of passive features being arranged to engage with at least one of the arrays of optically switchable molecular actuators disposed on the other of the bodies to thereby define the series of stepper positions. In at least one embodiment of the invention, one or more of the arrays of passive features includes an array of passive molecular elements which are not optically switched when any of the molecular actuators are switched. In at least one embodiment of the invention, at least one of the arrays of molecular actuators is arranged to change its state of engagement with at least one of the arrays of passive features when the said array of molecular actuators is optically switched. In at least one embodiment of the invention, the motor includes one or more of: at least three arrays of molecular actuators of different types: and at least two arrays of molecular actuators of different types and one array of passive elements.

In at least one embodiment of the inventive motor, each molecular actuator of each of one or more of said different types of molecular actuator includes a molecule from the class of azobenzene molecules. In at least one embodiment, each different type of molecular actuator including a molecule from the class of azobenzene molecules includes a different type of azobenzene molecule or moiety.

In at least one embodiment of the inventive motor, each molecular actuator of each of one or more of said different types of molecular actuator includes or is coupled to one or more a light-harvesting molecules or moieties. In at least one embodiment, the light-harvesting molecules or one or more of said different types of molecular actuator includes a BODIPY molecule.

In at least one embodiment of the inventive motor, each of one or more of the different types of molecular actuator is switchable using a different spectrum of light.

In at least one embodiment of the inventive motor, each of one or more of the different types of molecular actuator is switchable using a different envelope over time of intensity of light.

In at least one embodiment of the inventive motor, being optically switchable between at least two different molecular states includes being optically switchable between at least two different molecular conformations.

In at least one embodiment of the inventive motor, being optically switchable between at least two different molecular states includes being optically switchable between at least two different states of charge distribution.

In at least one embodiment of the inventive motor, each molecular actuator of each of one or more of said different types of molecular actuator is in communication with at least two light harvesting molecules.

At least one embodiment of the inventive motor further includes one or more light sources arranged to selectively optically switch the molecular actuators of each type.

In at least one embodiment of the invention, the motor further includes a controller arranged to control the one or more light sources so as to drive progressive movement of the first and second bodies relative to each other.

In at least one embodiment, the invention includes a plurality of motors wherein each motor includes a plurality of said types of optically switchable molecular actuators, each motor including at least one said type of molecular actuator in common with at least one other of the motors, each motor being drivable by a different combination of optical signals to each of the other molecular actuators. In at least one embodiment, the plurality of motors is arranged such that they all receive the same optical signals as each other. In at least one embodiment, each of the plurality of motors is arranged to provide a motor action including progressive movement along a different axis to each of the other motors. In at least one embodiment, the plurality of motors is coupled to a common mechanical load.

In another aspect of the invention, there is provided a method including providing first and second bodies in confrontation with each other and at least a first array of a corresponding first type of optically switchable molecular actuator, each array being fixed on one of the first and second bodies; providing repeated switching of the at least a first array to provide progressive movement of the first and second bodies relative to each other. In at least one embodiment of the method, the at least a first array includes at least two arrays each of a different corresponding different type of optically switchable molecular actuator, each array being fixed on one of the first and second bodies, the method including independently switching the molecular actuators of each type to provide said progressive movement. In at least one embodiment of the method, independently switching the molecular actuators of each type to provide said progressive movement includes repeating an ordered switching of each of the types of optical switchable molecular actuator. At least one embodiment of the method includes reversing the order of the ordered switching to provide progressive movement in a reverse direction. In at least one embodiment of the method, the repeated switching order includes at least three time intervals in each of which a different combination of none, one, or more than one of the different types of molecular actuator are activated. In at least one embodiment of the method, one or more of the types of molecular actuators includes an azobenzene molecule or moiety. In at least one embodiment of the method, each molecular actuator is switchable using a different optical signal, the different optical signals including one or more of different frequency spectra: and different intensity profiles over time.

In yet another aspect of the invention, there is provided a method including disposing one or more arrays of optically switchable molecular actuators between opposing bodies, and supplying a repeated sequence of optical signals which switch the molecular actuators so as to provide a progressive motor action between the bodies. In at least one embodiment of the method, the arrays of optically switchable molecular actuators are disposed between the opposing bodies in a configuration such that each repeated sequence urges the opposing bodies into at least three different alignments, each alignment corresponding to a different combination of none, one or more of said optical signals.

Yet another aspect of the invention provides the use of one or more different molecules, each of which is switchable between at least two different states by a corresponding control signal, as molecular actuators in a nanoscale stepper motor. In at least one embodiment of such a use, each of the one or more different molecules are optically switchable between at least two different states. In at least one embodiment of such a use, the molecules include one or more of: azobenzenes, aromatically linked pyridines, diarylethenes, dithienylethenes, stilbenes, spiropyrans, fulgides, and phenoxynaphthacene quinones. In at least one embodiment of such a use, one or more of the molecules are in communication with a light harvesting molecule coupling the corresponding control signal to the molecule.

The motor of FIG. 1 comprises first and second bodies 10, 20 which are located in confrontation with each other across an interface 30, and which are arranged to translate laterally relative to each other. This relative lateral movement is driven by a motor action provided by arrays of the optically switchable molecular actuators 40, 42 provided within the interface 30. The motor may drive the relative lateral movement along a single axis or path, either in one or both opposite directions along that path, along more than one axis or path or more generally within a two dimension space which may be flat or curved (for example if the bodies are concentric or coaxial), or in other ways. The motor drive will typically be used to provide a useful mechanical function X, for example to provide a micro-actuation or alignment function, for example for a molecular level 3D printer.

Each actuator 40, 42 is attached or fixed to one of the two bodies, and optical switching of an actuator is used to change its state of interaction with the other body to which it is not attached. Of course, not all such optical switching actions need give rise to a change in state of interaction, as this may depend on the current configuration of the motor, for example the current relative positions of different types of actuator and other features. Switching of an actuator may comprise changing the molecular configuration and/or one or more other physical and/or chemical properties of the actuator between two or more different states of the actuator, thereby giving rise to changes in the state of interaction with the other body.

In FIG. 1 the actuators are shown as being of two different types A and B, but just one, or more than two different types of actuators could be used. By controlling the timing of optical actuation of the different types of actuators the motor drive is provided. The different types of molecular actuators may be provided by various different molecules, molecular classes, functional groups and so forth. In detailed embodiments described below, for example, actuators are provided by azobenzene class molecules, which may each be coupled to one or more light-harvesting antenna molecules, or to a number of such light-harvesting antenna molecules shared among several actuators.

Molecular actuators of a particular type switch together when triggered by a suitable optical signal 50, 52 with which the motor is illuminated, for example using one or more lasers, laser diodes or other light sources. The spectral characteristics of the optical signals will depend on the nature of the molecular actuators to be switched, but might typically be relatively monochromatic, in the range of about 450 nm to 800 nm. Where narrow band light sources are used, for example to selectively switch particular types of actuator, these could have band widths of up to about 50 to 100 nm.

The different types of molecular actuators can be switched independently of each other by the use of optical signals with different properties, for example optical signals with different profiles of wavelength/frequency of the light, intensity, polarisation, direction of incidence, and combinations of these and other properties and envelopes of such properties over time, thereby being dependent for example on duration. For example, one type of actuator may be switched by a short duration pulse of higher intensity light, while another type may be switched by a longer duration pulse of lower intensity light, and so can be independently switched even if the frequency bands or profiles of light used for the switching are the same or overlapping. Such types of molecular actuators may include actuators which can be differentiated by rates of deactivation, for example thermal deactivation, in which a type A is activated by a short, intense pulse of light of insufficient integrated flux to activate a type B, but type A quickly inactivates if unilluminated. Type B then requires more integrated flux for activation, and as a consequence can be activated by a longer, lower intensity pulse that does not activate type A. Note that these time based effects can introduce an asymmetry between a sequence of activation A-B and a reverse sequence B-A that could enable the motor to step in one direction but not the reverse direction.

In the arrangement of FIG. 1 the type A actuators are switched using a first optical signal 50 and the B type actuators are switched using a second optical signal 52. A single optical signal could be used to switch a particular type of actuator, with the interaction state of the actuator depending on whether the optical signal is present or absent, two different optical signals could be used to toggle in each direction between the two states of an actuator type, or various other possible schemes may be used.

The switching of the actuators will typically be statistical in the sense that not all actuators of a particular type will necessarily be switched by a particular optical signal, and some actuators of one or more other types may be unintentionally switched by the same optical signal. The operation of the motor may thereby be governed by an average effect over a large number of actuators of one or more different types. Preferably however, a majority or substantially all of the actuators of a particular type are switched as intended by their corresponding driving optical signal(s).

In detailed embodiments described below, the different optical signals may be provided by laser light of different frequencies, each such frequency being chosen to cause switching of a respective type of actuator. Depending on the type of molecular actuators used, the actuators may be considered to be either in an activated or deactivated state, for example in an activated state in which their molecular configuration causes them to interact, or interact more strongly, with the opposing body, and in a deactivated state in which their molecular configuration causes them not to interact or to interact more weakly with the opposing body.

Although some types of molecular actuators may have two states between which they can be optically switched, for example between activated and deactivated states, other types of molecular actuators may have more than two such states, or a continuum of states, transitions between these states being provided by suitable optical signals, and references to switching of the molecular actuators between states should be understood accordingly.

It should be noted that, although it is optical actuation and switching of the molecular actuators that is largely described in this document, the invention also applies where different mechanisms are used in addition or instead of optical activation, for example switching or activation using thermal signals, pressure signals, acoustic signals, magnetic field signals, electric field signals or chemical signals (for example by changing concentration of trigger molecules). Actuation and switching may also or instead be performed using electromagnetic radiation other than optical radiation such as millimetre and longer waves including microwave and radio waves, as well as other sorts. When we refer to optically switchable actuators we are referring to the use of electromagnetic radiation in the ultraviolet and infrared regions, as well as visible radiation.

The optically switchable molecular actuators may be distributed in regular or irregular arrays across some or all of the interface between the first and second bodies. Each such array may be fixed either to the first or second body, although in FIG. 1 the arrays of both type A and B are shown as distributed across only the first body. One or more of the arrays may be essentially one dimensional, i.e. linear, although more typically two dimensional arrays can be used. A regular array of molecular actuators may, for example, comprise a one or two dimensional array of such actuators with a substantially regular spacing or repeated pattern of such regular spacing between the actuators. The spacing or pattern of spacings in one dimension could be different to the spacing in another dimension, and in two dimensions the pattern of spacings may be rectilinear, skewed rectilinear, hexagonal, or take other regular forms.

The distribution of the actuators in arrays may also be statistical in the sense that not all actuators of a particular type will be in a regular position of the array, and actuators maybe missing from some positions of the array, and so forth. The operation of the motor may therefore be governed by the actuators being positioned as a regular array as an overall or average effect.

Figure 2:
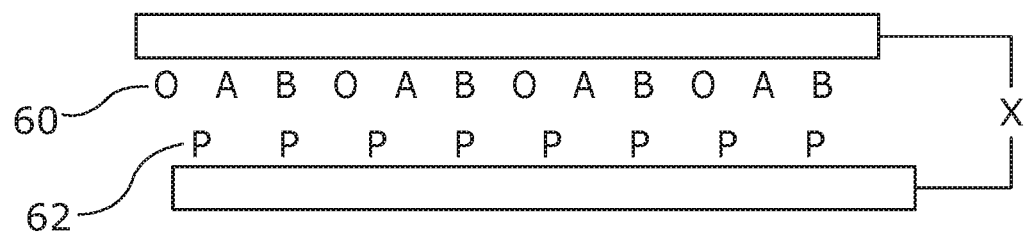
FIG. 2 is similar to FIG. 1, but adds passive features such as passive molecular elements O and P in the interface to contribute to one or more distinct alignments of the motor.

In FIGS. 1 and 2 the different types of molecular actuators are interleaved, in the sense that the arrays are intermingled on a single surface, while each array retains a required periodicity, so that along the axis of movement of the motor a sequence changing periodically between type A and B, and back again is seen. This interleaving could of course comprise of a single alternating sequence of single instances of each type as in A-B-A-B, or could include multiple adjacent instances of one or both types as in A-A-A-B-B-B-A-A-A-B-B-B and so forth.

Such interleaving of arrays of different actuator types may also or instead be in another direction, for example in an axis oblique or perpendicular to the axis of movement. In this way, runs of a single type of actuator in the axis of movement could alternate between different types of actuator in a perpendicular direction.

The described motors may also be implemented without interleaving of the arrays of actuators. For example, homogenous blocks of each type of actuator could be used.

Although interleaving may give rise to convenient working arrangements, a more general requirement is that the actuators, and if present passive features described below, are distributed so as to provide a repeating sequence of alignments between the bodies, wherein applying suitable optical signals drives the bodies between the alignments to provide the required motor action. To this end, a suitable spatial periodicity with respect to displacements of the actuators and passive features, and/or interactions between the actuators and the passive features, is required to provide a bulk motor action.

As illustrated in FIG. 2, the molecular motor may also comprise one or more arrays of passive features, each array being a regular or irregular array of such passive features. These passive features provide a structure with which switching of the actuators may interact in order to provide the motor drive, although actuators may also interact with other actuators, for example with actuators of the same or different type.

To this end, an array of passive features may be provided in various ways such as a repeating profile or potential field for example of energy, charge or binding affinity or other aspects of a surface of one of the bodies, or by passive molecular elements which have been fixed or attached to one of the bodies and which give rise to the same or similar effects. To this end, passive features may operate using interactions such as hydrogen bonding, hydrophobic interactions, steric/mechanical interference, and in other ways.

Two arrays of passive features are shown in FIG. 3 as types O and P. Each such array of passive features may thereby provide or contribute to a structure to interact with one or more other arrays either of optically switchable molecular elements, and/or one or more other arrays of passive molecular elements.

The passive features 60, 62 may thereby provide one or more functions supporting operation of the molecular motor. For example, one or more arrays of passive features 60, 62 may define, by interaction with one or more other arrays of passive features or molecular actuators, a series of positions between the first and second bodies. Optical switching of the molecular actuators may then be used to drive the molecular motor from one stepper position to the next. One or more arrays of passive features 60, 62 may also provide a reference structure on which one or more arrays of molecular actuators may act as they switch to drive the motor.

As already discussed in respect of the molecular actuators, the passive features, which may be passive molecular elements, and which are not optically switchable or are not optically switched by the optical signals used to switch the molecular actuators, may be distributed in arrays, preferably regular arrays, across some or all of the interface between the first and second bodies, each array being fixed to either the first or second body, and having various possible one or two dimensional arrangements as already discussed in respect of the molecular actuators.

The motor action to drive lateral movement between the first and second bodies 10, 20 is provided by sequential or ordered switching of the different types of molecular actuators 40, 42, by providing a suitable sequence or order of optical driving signals 50, 52. If there are two different types of molecular actuators then these can together be put into one of four interface states using the optical driving signals: both types either activated or inactivated, or only either one of the actuators activated. By providing one or more suitably spaced arrays of passive molecular elements with which the molecular actuators can interact depending on the relative positions of the first and second bodies, cycling through different ones of these states can drive the motor action. One example of how this may be achieved is illustrated in FIGS. 3A-3D, in which a mechanical style of interaction is used as an analogy for corresponding molecular scale interactions (note that some molecular interactions which may be used in the invention are also mechanical/steric). Some other configurations which can be used to provide a required motor action will be discussed later in this document.

Figure 3A:
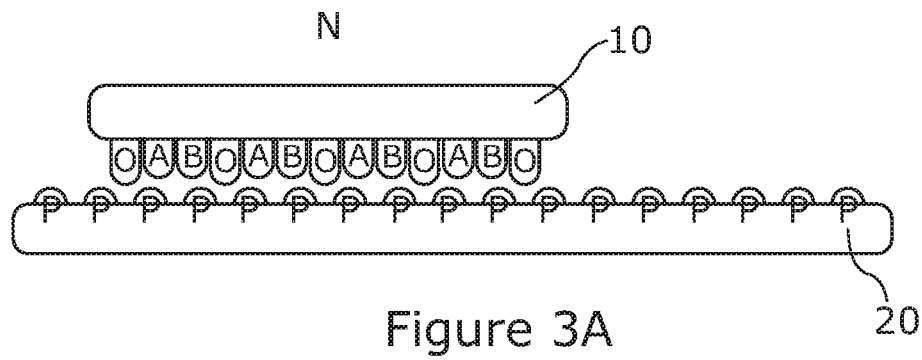
FIGS. 3A to 3D show, using a mechanical paradigm for alignment forces, how the motor devices of FIGS. 1 and 2 may operate a progressive stepwise motion by serial activation of the molecular actuators.
Figure 3B:
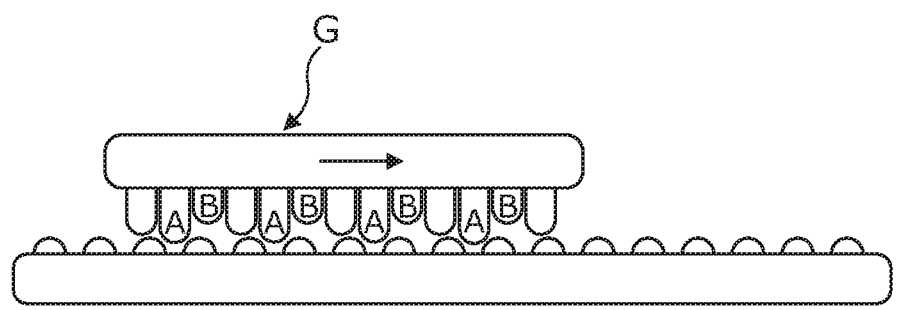

Referring first to FIG. 3A, the first body 10 carries arrays of molecular actuators of types A and B which are interleaved with each other and with an array of passive features O also carried by the first body, to form a sequence OABOA-BOAB . . . . The second body carries an array of passive features P. In FIG. 3A the molecular actuators A and B are each in a first state. The first and second bodies are in a stepper position in which the relative position of the two bodies is defined by a particular interaction between the arrays of features O and P. In the figure, the spacing of the array of features O is twice that of elements P, so that the spacing between each element/feature O-A, A-B, B-O is two thirds that of the spacing between the features P.

Other spacings with the same or a similar effect are also suitable. For example, in FIG. 3A it can be seem that omitting half of the actuators of type A and/or type B, and/or half of the passive features O would lead to the same pattern of interactions with respect to displacement, but with fewer of the features P being engaged in a particular step. These may be irregularly spaced, or interact with separate but approximately parallel arrays P. In general, any arrangement that has the property that interaction between O and P will enable a shift in alignment on activation of A, then a further shift in alignment on activation of B, etc. may be used. Overlapping activation of A and B may also be advantageous. Note that the spacing of features OP can determine the step size, and this spacing can be smaller, sometimes much smaller, than the spacings of features O, A and B, and so forth.

In FIG. 3A no optical signals are being used to switch the actuators, so the optical signal may be said to be in a null state N. Starting from the stepper position of FIG. 3A, in FIG. 3B a first optical signal G is used to switch the molecular actuators of type A, causing them to change their state of interaction with the second body 20, and in particular with the array of passive features P carried on that body. An effect of this change of state is that the relative positions of the first and second bodies changes, with the first body moving to the right of the figure and/or the second body to the left.

Figure 3C:
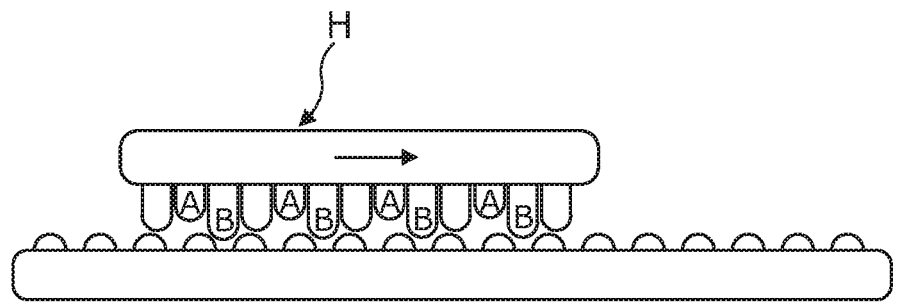

In FIG. 3C the first optical signal G is removed, allowing the actuators of type A to switch back to their previous state, and a second optical signal H is used to switch the molecular actuators of type B to change their state of interaction with the second body 20, and in particular with the passive features P carried on that body. An effect of this change of state is that the relative positions of the first and second bodies change again, with the first body moving to the right of the figure again and/or the second body to the left.

Figure 3D:
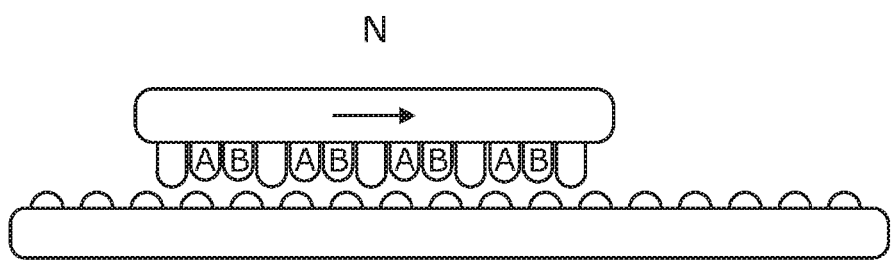

In the FIG. 3D the second optical signal H is removed, thereby returning to the null optical signal state N, so that both types of molecular actuator are then in the original state of FIG. 3A, the first and second bodies are in a relative stepper position, but the new stepper position is one spacing of the passive features P from the original stepper position. The sequence of optical signals N-G-H-N can be repeated to provide successive steps of movement, and can be reversed N-H-G-N to provide a movement in the reverse direction.

Repeating the optical signal sequence N-G-H-N-G-H-N . . . therefore gives rise to progressive movement of the bodies relative to each other in a particular direction, in this case in the direction shown by the arrows in the body 10. This optical signal sequence corresponds to an ordered switching of the different types of optically switchable molecular actuator in a particular order O-A-B-O-A-B . . . where O represents actuation of neither A nor B. It can also be seen that by reversing the optical signal sequence to give N-H-G-N-H-G-N . . . and therefore the order of switching to O-B-A-O-B-A . . . a progressive movement of the bodies relative to each other in the opposite direction is achieved. Such optical signal sequences can also be interleaved with sequences that drive other proximal motors, as described below.

Depending on the number of different types of optically switchable molecular actuator, the number and nature of states of each actuator, and the details of the one or more arrays of passive elements, a variety of different orders and combinations of switching of actuators may be used to achieve a desired motor action in one or more than one direction.

Considering just a one dimensional motor action for now, an array of just one type of actuator may be used to achieve a motor action in one direction. For example, an array of actuators A triggered to switch between two states may drive a motor action in one direction if an array of passive features with a suitable interaction profile is provided. A suitable interaction profile could for example provide a sawtooth type profile in which actuation A lifts the interaction between the bodies over the steep slope of the sawtooth, and a null state allows the interaction to move to the start of the next steep slope. Such a motor could thereby be driven with an actuation order written as A-O-A-O . . . Such a motor could also provide progressive movement in a choice of two directions by control or adaption of the array of passive features to provide different interaction energy profiles.

If there are two different types of molecular actuators then these can together be put into one of four interface states using two optical driving signals: both types either activated or inactivated, or only either one of the actuators activated, and these states could be written as O, AB, A and B. The arrays of actuators A and B, and any arrays of passive features, may then be structure to provide progressive movement in response to a repeated switching between at least three combinations, for example in the orders O-A-B-O . . . (as in FIGS. 3A-3D) but also in the orders O-A-AB-O . . . , O-AB-A-O . . . , A-AB-B . . . , O-A-B-AB-O. If a single type of actuator has more than two states, for example states O, A and B, progressive movement can be provided in the same way by switching between the three states O-A-B-O. All of these orders may be reversible to provide progressive movement in a reverse direction, if the interactions have suitably shaped profiles to allow this.

If there are three different types of actuators then these can give rise to driving orders such as O-A-B-C-O.

More generally, a reversible progressive motor action may be attained where the optically switchable molecular actuators and passive features provide at least three stable alignments of the opposing bodies under different combinations of activation. One such alignment may be provided by an absence of activation, as in the null optical signal N described above, and other different alignments are provided by different optical signals. Repeating a sequence of three different optical signal combinations (optionally including a null signal) can then give rise to the desired progressive motion.

Figure 4:
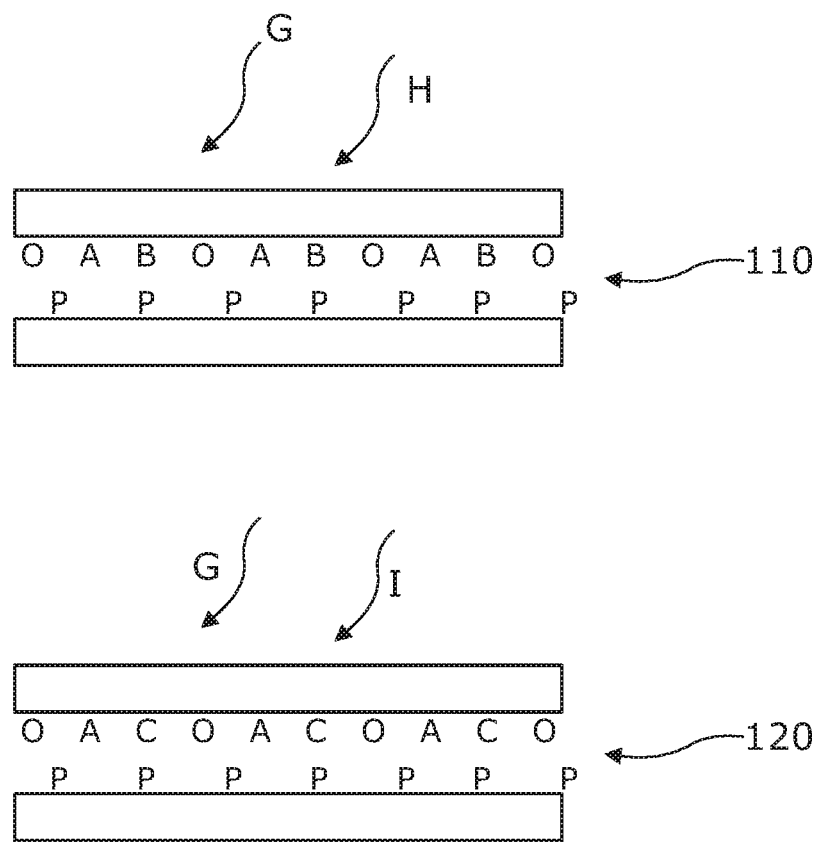
FIG. 4 shows how two co-located motors may be independently operated by suitable selection of optical driving signals.

If a first motor is driven by two optical signals G and H, and a second motor using the same types of molecular actuator receives the same optical signals, for example because of proximity to the first motor, then both motors will operate under control of the signals G and H. However, if as shown in FIG. 4 the two motors 110, 120 use different sets of types of molecular actuator then they can be controlled independently. In FIG. 4, the first motor 110 uses a sequence of molecular actuators A-B-A-B (with interleaved passive features if required), whereas the second motor 120 uses a sequence of molecular actuators A-C-A-C (again with interleaved passive features if required).

It can be seen that the first motor 110 of FIG. 4 may be driven by a sequence of optical signals O-G-H-O-G-H-O (or the reverse) and the second motor 120 may be driven by a sequence of optical signals O-G-I-O-G-I-O (or reverse). The first sequence may cause some reciprocating movement of the second motor, and the second sequence may cause some reciprocating movement of the first motor, but these reciprocating movements do not lead to a motor moving progressively between stepper positions so do not cause a driving action.

Figure 5:
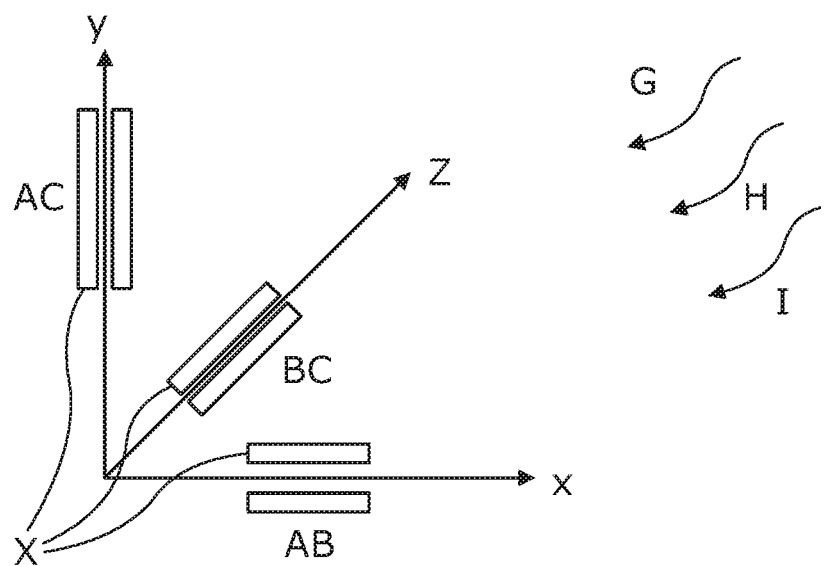
FIG. 5 shows how the independent operation of FIG. 4 may be used to for a multi-axis driving mechanism.

If, as shown in FIG. 5, the two motors 110 and 120 are aligned along different axes, but subject to the same driving signals G, H, I, then they can be used to provide a multi-axis driving action, for example by being coupled to a common drive action X. As shown in FIG. 4, two of the motors can be driven using three different optical signals, and as also shown in FIG. 5, three motors and therefore a three-axis driving action can be also be effected using three different driving signals, with pairs of signals G,H; H,I and G,I being used to drive each of the three motors respectively. Such a scheme can easily be extended to larger numbers of motors, with correspondingly suitable numbers of actuator types and optical driving signals.

Figure 6A:
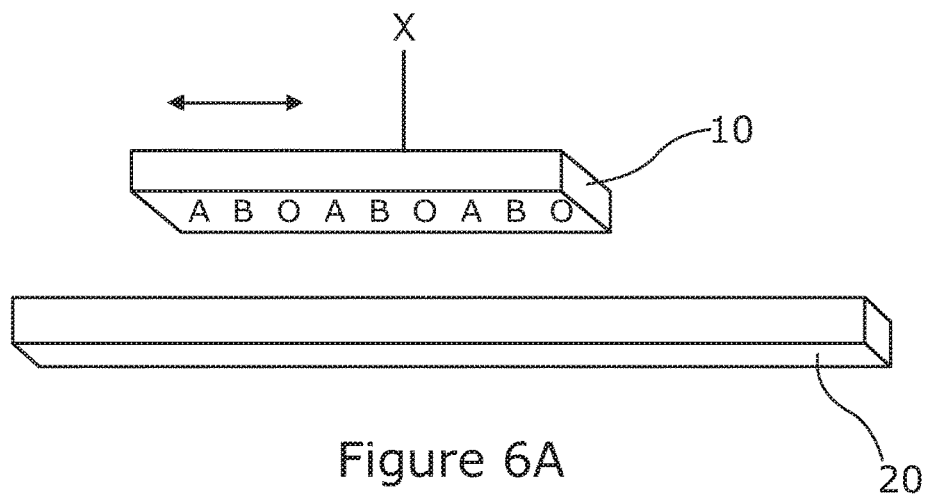
FIGS. 6A-6C illustrate different arrangements of the opposing motor bodies, molecular actuators and passive features.

A single motor according to the invention may be provided in various different configurations. For example, in FIG. 6A, the two opposing bodies 10,20 are elongate and one may be significantly shorter than the other. For example, the longer body could be a fixed body and the motor action used to drive movement of the shorter body as a shuttle to along the longer body to provide mechanical action X.

Figure 6B:
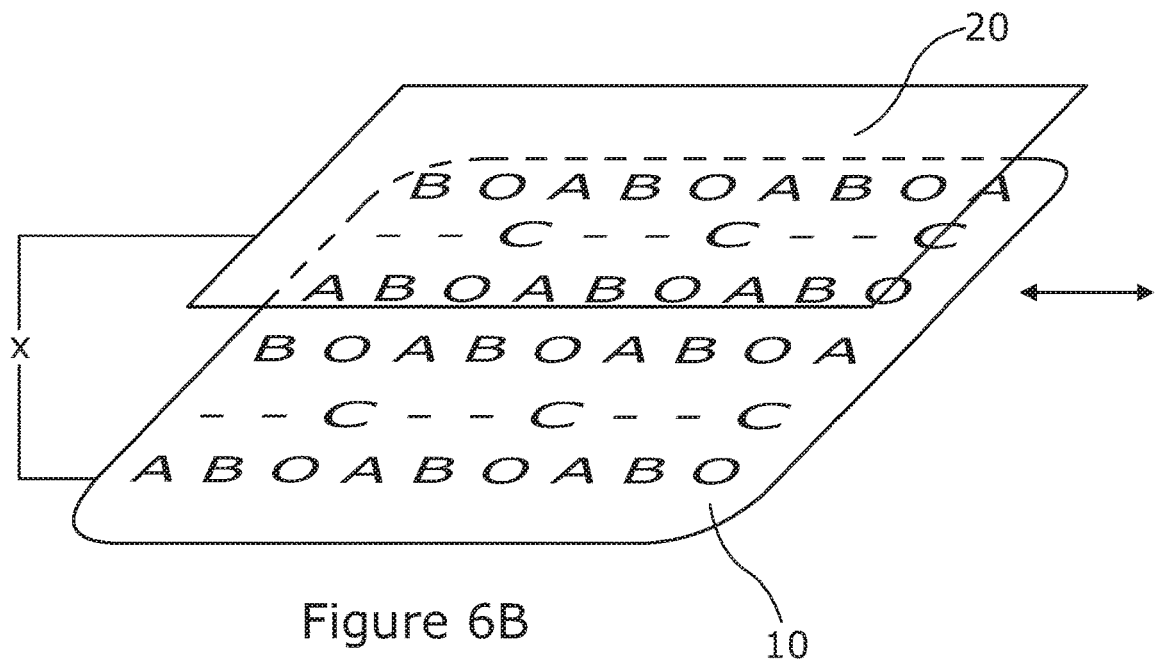

In FIG. 6B the first and second bodies are both substantially planar, and the arrays of actuators are distributed across the planar interface. Additionally in FIG. 6B, a first axis of motion is provided by multiple parallel sequences of molecular actuators and passive features A-B-O-A-B-O, and a second of axis of motion (in this case perpendicular to the first axis) is provided by multiple parallel sequences A-C-O-A-C-O, so that this single motor can be driven independently in at least two different axial directions using different sequences of optical signals to provide mechanical action X.

Figure 6C:
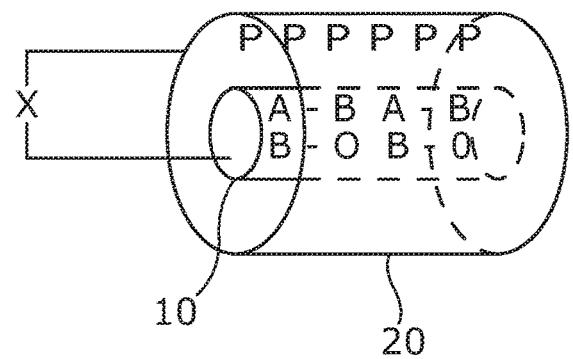

In FIG. 6C the two bodies 10, 20 are coaxial or concentric, for example being circular or cylindrical, and the relative lateral motion at the interface 30 between the bodies thereby also gives rise to a relative rotational motion between the bodies, driving a rotational mechanical action X. Helical arrays could be used to drive a helical or screw-like motion in which the axial displacement can be smaller than the step size along the array.

The various motors described above may be used to provide a mechanical driving action by coupling the bodies to components of a system to thereby cause displacements that move one component with respect to another in discrete steps. Potential systems include, for example, arrangements in which active elements are positioned with respect to a surface to enable lithography of the kind demonstrated in scanning tunneling and atomic force microscopy, with advantages stemming from the possibility of providing larger numbers of nanoscale positioning devices according to the present invention.

Figure 7:
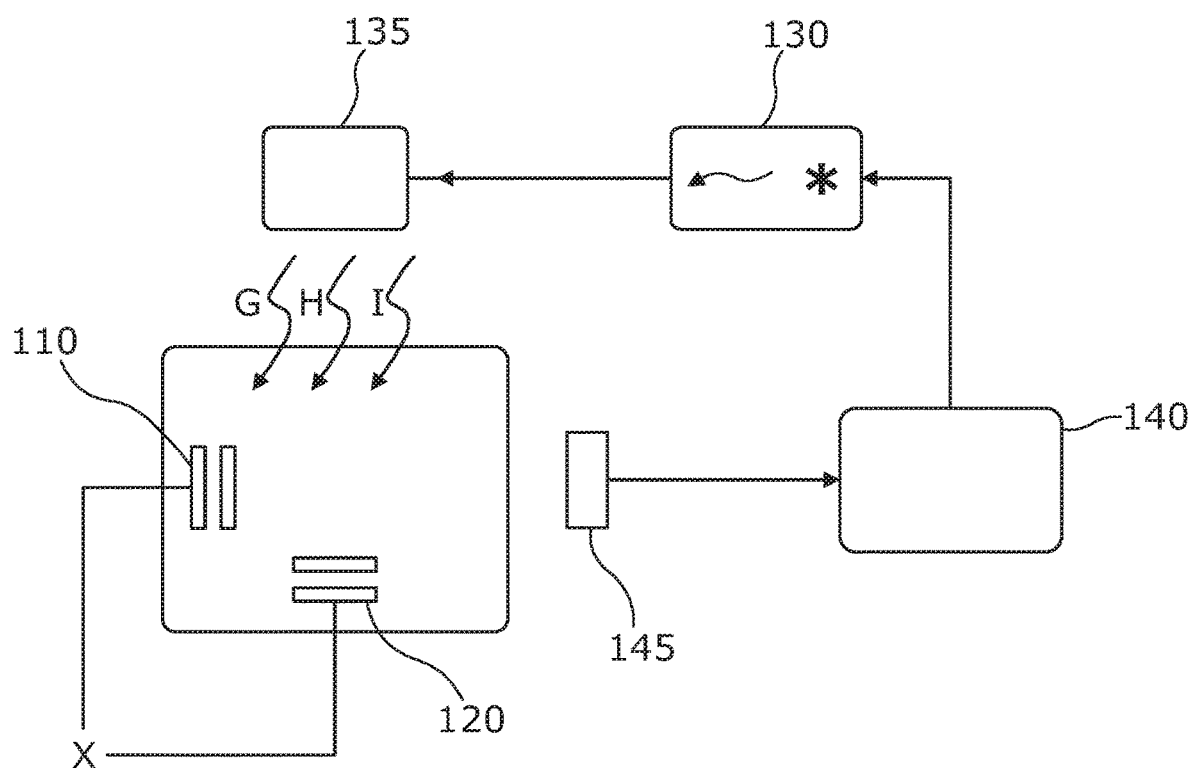
FIG. 7 illustrates an implementation of molecular motors in a system comprising light sources and optics to generate the optical driving signals, and feedback control.

Referring now to FIG. 7 there is shown schematically an implementation of one or more molecular motors as described above, which together provide a mechanical driving action X. In this figure, motors 110, 120 are coupled to the driving action X to provide a mechanical function in one or more directions or axes of translation, and this action along each axis is preferably reversible as described above.

The motors 110, 120 are controlled using a light source 130, which could be provided by one or more lasers, light emitting diodes or similar, which provides optical signals G, H, I to the molecular motors 110, 120 through optics 135 in order to provide the driving action X as already discussed above. A controller 140 provides electrical driving signals to the light source 130 in order to control the timing and sequence of optical driving signals required to effect the desired the driving action. One or more sensors 145 may be used to obtain feedback from the molecular motors and/or the driving action in order for the controller 140 to more accurately provide the desired driving action X.

Whether or not used to provide feedback as mentioned above, one or more sensors 145 may for example measure relative or absolute movement or position of one or both of the opposing bodies, or of mechanical structures suitably coupled to those bodies to reflect such movement. Such sensors could thereby confirm correct or incorrect movement or alignment of the bodies. In some embodiments, fluorescence resonance energy transfer could be used to confirm a particular alignment, thereby providing sensing indicating the alignment of two bodies from the position dependent fluorescent signals.

Some particular examples of molecules and molecular structures which may be used to provide the different types of molecular actuators will now be described. Broadly speaking, the optically switchable molecular actuators may comprise any molecules that change configuration or interaction with other structures when irradiated with the corresponding wavelength of light. A change in configuration could comprise a change in conformation, i.e. shape, but could also or instead comprise a other changes such as a change in binding affinity, dipole moment, electric charge, and so forth, including a variety of different physical and/or chemical properties.

Figure 8:
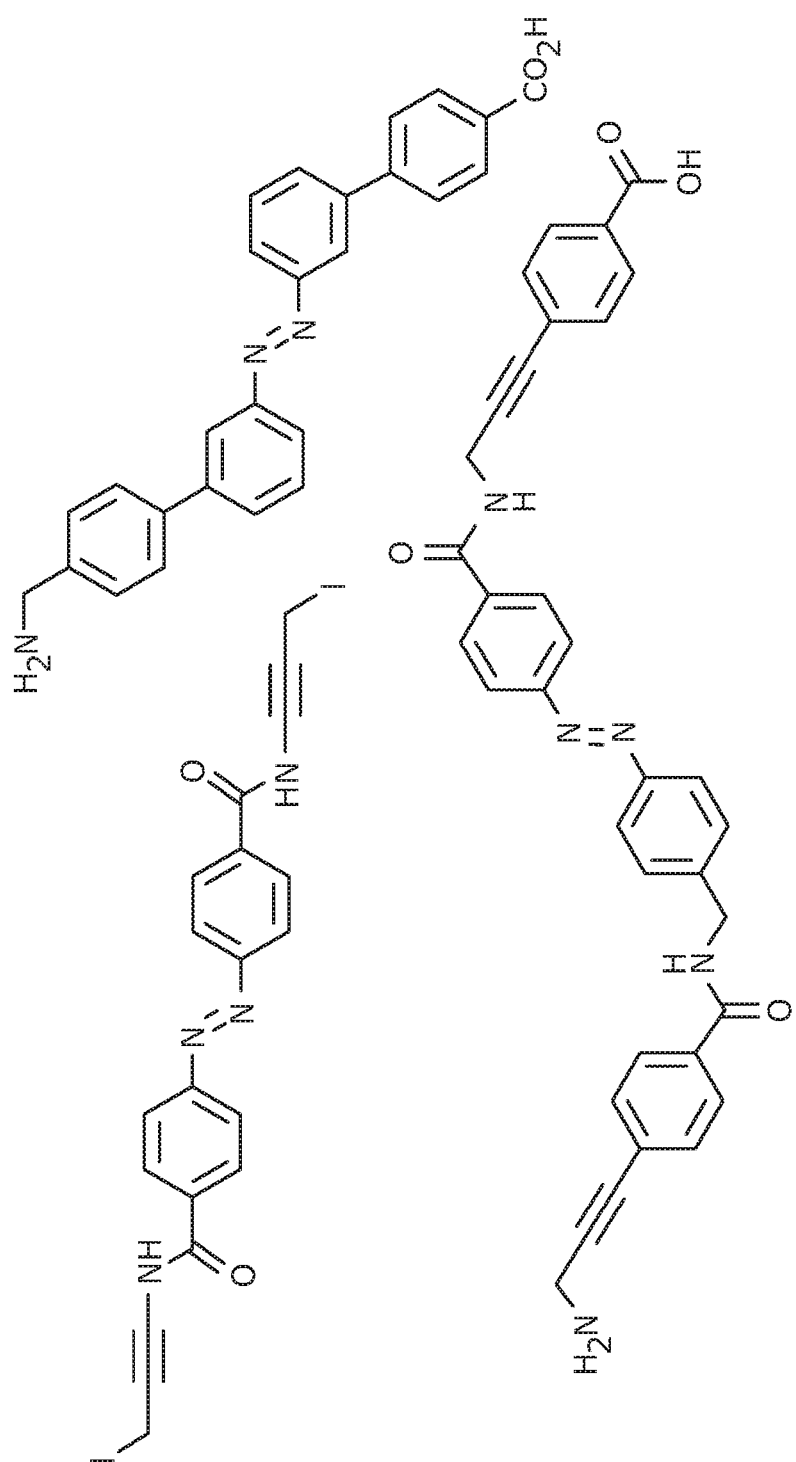
FIG. 8 shows some azobenzene molecules which may be used as molecular actuators.
Figure 8:
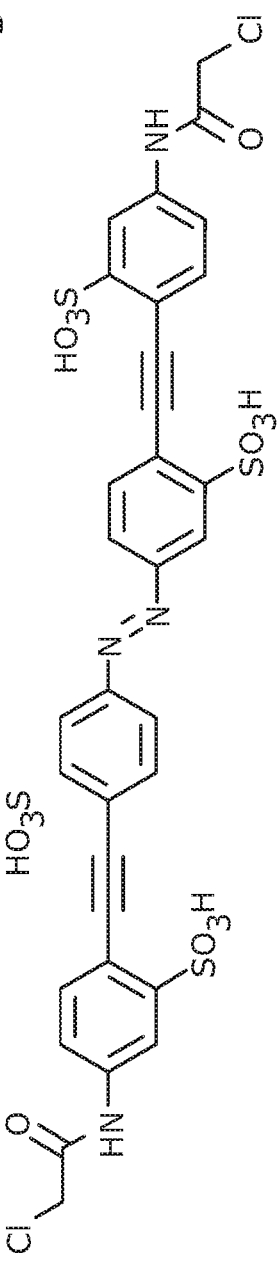

In one embodiment, the actuators may be molecules in the class of azobenzene-like molecules, a class commonly referred to in the scientific literature as "azobenzenes" (referred to here generally as azobenzenes). For example, where an azobenzene molecule is used, it may be bound to one body in such an orientation that it does not interact with the other body when in the E configuration but it can interact with the other body when in the Z configuration. On exposing the azobenzene molecule to the correct wavelength of light, it changes configuration from the E form to the Z form. As the Z form can interact with the other body, possibly with a molecule bound to the other body, the activation of the azobenzene to the Z form causes lateral movement of the body to which it is bound relative to the other body in order for the azobenzene to interact more favourably with the next site on the other body. Some examples of suitable azobenzene molecules which may be used to provide different types of molecular actuator are shown in their E configuration in FIG. 8.

Other molecules which could be used to provide a suitable optically switched conformational change include other azo-linked aromatics such as pyridine, diarylethenes, dithienylethenes, stilbenes, spiropyrans, fulgides and phenoxynaphthacene quinones. Molecules which could be used to provide a suitable optically switched electric charge change include photoacids and structures in which charge is transferred within or between molecules, or to an adjacent conductor or semiconductor. Various molecules could be used to provide a suitable optically switched dipole or higher order electric moment (i.e. intramolecular charge transfer). For example, photoinduced charge separation in retinyl-C60 dyad at microsecond time scales, or photoinduced charge separated states of fullerene-donor molecular systems may be used. Charge transfer mechanisms which may be used also include those of Ru(II)-bipyridine complexes or tetrathiofulvalene-perylene dyads in supramolecular systems, devices and machines.

One or more types of molecular actuator may be connected to a further molecule or moiety which acts as a light-harvesting antenna or to otherwise change the optical response characteristics of the molecular actuator. For example, many azobenzene molecules absorb light over a broad spectrum. Connecting a particular azobenzene or other molecule to a particular light-harvesting antennae with narrower absorption spectra therefore provides a molecular actuator which is more wavelength specific, i.e. responds to a narrow frequency band of optical driving signal light. In this way, a particular molecule or class of molecule with a broad spectral response can be used to provide a plurality of different types of molecular actuator each with a narrower spectral response with reduced or minimal overlap with each other.

Figure 9:
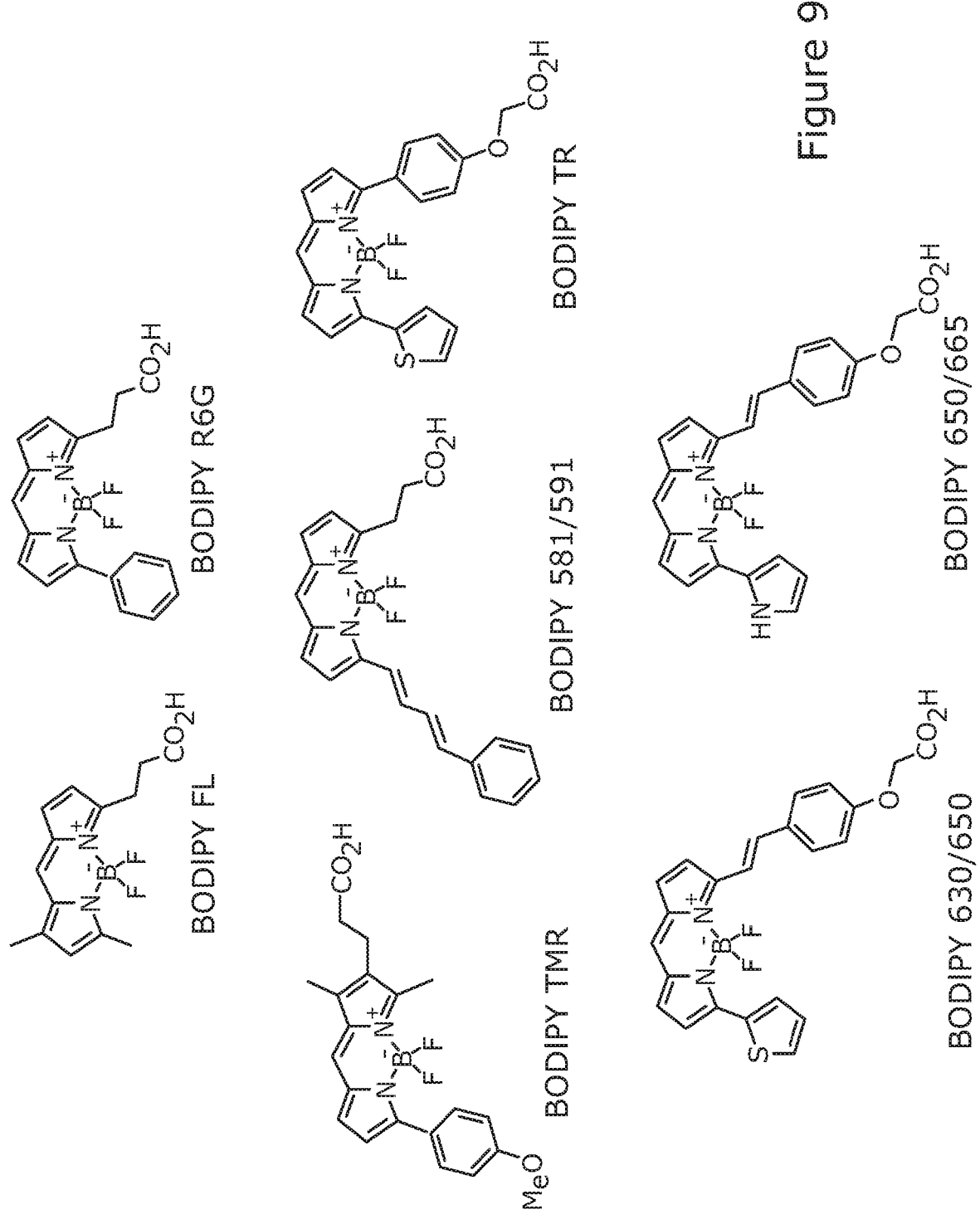
FIG. 9 shows some BODIPY® (boron-dipyrromethene) dyes which can be used as light harvesting antennae.

Example of suitable light harvesting antenna molecules or moieties are members of the class of BODIPY® (boron-dipyrromethene) dyes as they have strong narrow absorption bands at a range of frequencies. Other examples include carotenoids, proteins and a combination of (BODIPY®) dyes covalently linked to pyrene. A light harvesting antenna may comprise one or more light harvesting molecules such as BODIPY® molecules or moieties. For example, more than one (BODIPY®) molecule may be used to form a dendrimer which may comprise for example, two, three or more BODIPY molecular units, as demonstrated in Yilmaz et al., "Light harvesting and efficient energy transfer in a boron-dipyrrin (BODIPY®) functionalized perylenediimide derivative", Org. Lett., 2006, 8 (13), pp 2871-2873, and in Yuan et al., "Light Harvesting and Efficient Energy Transfer in Dendritic Systems: New Strategy for Functionalized Near-Infrared BF2-Azadipyrromethenes", Chemistry—An Asian Journal, Volume 4, Issue 5, pages 707-713, May 4, 2009. The energy transfer to the molecular actuator such as an azobenzene can be effected by proximity and fluorescence resonance energy transfer or by a covalent linkage. A range of BODIPY® dyes which can be used for these purposes is shown in FIG. 9. Noncovalent binding to multiple dye molecules in proximity to one another and to the actuator may also be used, demonstrated in Miller et al., "Self-assembling light-harvesting systems from synthetically modified tobacco mosaic virus coat proteins", J. Am. Chem. Soc., 2007, 129 (11), pp 3104-3109.

Note that a single light harvesting structure such as one or more molecules or moieties could be shared by a plurality of optically switchable molecular actuators coupled to the light harvesting structure, for example shared by part or all of an array of such actuators of a particular type. In this way, excitation energy can be transferred among antenna molecules until one of the coupled actuators absorbs the energy and undergoes a state change.

To form regular arrays of optically switchable molecular actuators or passive molecular elements, the underlying surface of the respective body may first be modified to present a regular array of binding structures chosen or constructed to bind to the actuators or passive elements respectively. These binding structures could be provided by suitably engineered proteins, modifications of naturally occurring proteins, or in other ways. The arrays could be two dimensional, distributed across the appropriate surface, or effectively one dimensional, for example distributed along a linear structure such as the surface of a nanotube.

The attachment of regular arrays of protein molecules to surfaces to form two-dimensional crystals, for example, is discussed in McMillan et al., "A Self-Assembling Protein Template for Constrained Synthesis and Patterning of Nanoparticle Arrays", J. Am. Chem. Soc., 2005, 127(9), pp 2800-2801. Bacterial S-layer proteins, in particular, form a wide range of stable two-dimensional arrays that can be used as a basis for the arrays of actuators and/or passive elements. Such arrays of S-layer proteins are described in: Sleytr et al., "S-Layers as a basic building block in a molecular construction kit", FEBS Journal, volume 274, Issue 2, pages 323-334, January 2007; in Ilk et al., "Surfaces functionalized with self-assembling S-layer fusion proteins for nanobiotechnological applications", Colloids and Surfaces A: Physicochemical and Engineering Aspects, Volume 321, Issues 1-3, 15 May 2008, Pages 163-167, Organized Molecular Films Selected papers from LB12—the 12th International Conference on Organized Molecular Films, Jul. 1-5, 2007, Krakow, Poland; and in Sleytr et al., "Nanobiotechnology with S-layer proteins as building blocks", Progress in Molecular Biology and Translational Science, 103, pages 277-352, 2011. Each of these documents in incorporated herein by reference for all purposes.

Arrays formed on nanotube surfaces are described in Grigoryan et al., "Computational design of virus-like protein assemblies on carbon nanotube surfaces", Science, 332 no 6033 pp 1071-1076, May 2011. This document is incorporated herein by reference for all purposes.

Engineering novel or existing biological proteins to provide sites that bind specific organic molecules in specific positions and orientations is a known technique. These include molecules with relevant physical properties which may be used for molecular actuators, passive elements, and light harvesting structures in the present invention. Such engineered binding sites are described in: Tinberg et al., "Computational design of ligand-binding proteins with high affinity and selectivity", Nature 501, 212-216, 12 Sep. 2013; A. Skerra "Alternative binding proteins: Anticalins harnessing the structural plasticity of the lipocalin ligand pocket to engineer novel binding activities", FEBS Journal, Volume 275, Issue 11, pages 2677-2683, June 2008; and Lopes et al., "Computational design of protein ligand binding: Modifying the specificity of asparaginyl-tRNA synthetase", Journal of Computational Chemistry, Volume 31, Issue 6, pages 1273-1286, 30 Apr. 2010. For example, S-layer proteins can be modified to include structures that can provide the additional functional capabilities required to implement the invention. See: Tang et al., "Recognition Imaging and Highly Ordered Molecular Templating of Bacterial S-Layer Nanoarrays Containing Affinity-Tags", Nano Lett., 2008, 8 (12), pp 4312-4319, and Ilk et al., "S-layer fusion proteins construction principles and applications", Current Opinion in Biotechnology, Volume 22, Issue 6, December 2011, Pages 824-831. Each of these documents is incorporated herein by reference for all purposes.

The ability to modify surfaces of the bodies of the described motor with regular arrays of protein molecules that can be used to bind actuator molecules provides the ability to implement regular arrays of molecular actuators suitable for implementing the invention.

The passive features discussed above may be provided in various ways, including forming the arrays using techniques mentioned above. More generally, profiles across the surface of one or both opposing bodies, of physical and/or chemical characteristics with which the molecular actuators are able to interact selectively depending on their switched state, may be used. Such physical and chemical characteristics include electrostatic charge, dipole moment, hydrogen bonding and other types of binding affinity, and so forth, as well as mechanical interaction (steric) repulsion forces. Such profiles may be provided by periodic structure or characteristics of one or both bodies, or by passive molecular elements attached to one or both bodies in a periodic manner such as in an array. Such passive molecular elements could be provided by molecules or moieties with charged groups, hydrogen bonding groups, sterically bulky groups, or various other groups suitable for providing molecular interactions.

Passive features could also be implemented using bare or minimally modified surfaces of a silicate material, such as a mica or clay mineral, or the surface of a silicate nanotube such as of imogolite or germanium-imogolite. Such silicate surfaces can be selected to naturally bear regular arrays of charge to provide the passive features. Alternatively, such silicate surfaces could be chemically modified to bear regular arrays of molecular functional groups. The silicate surfaces can provide fine grained arrays of passive features that are well suited for use in stepper motors of the present invention.

Planar surfaces may be used to provide two dimensional arrays of passive elements, enabling use of arrays of actuators consisting of rows of alternating types, thereby placing many actuators in a compact configuration. On the other hand, silicate nanotubes may be used to provide one dimensional arrays of passive elements, providing elongate, rod shaped bodies of the motors, which undergo displacements through the described motor actions with respect to another, confronting body of the motor which may be implemented as a planar surface or as another elongate, rod shaped body.

The motor bodies could be provided by a variety of structures and materials. For example structural backbones such as silicon wafers, or nanotubes of silicate or carbon could be used, as could amyloid or other protein or peptide assemblies, or monolayers of any of a wide range of molecules bound to a wide range of surfaces. Spacing between individual molecular actuators may be larger than the step or stepper distances, for example using multiple arrays with small offsets. Lithography techniques may be used to position the molecular actuators and/or passive features. Multiple molecular actuators may be arranged to provide wide potential wells.

The molecular actuators, and passive features, may be distributed in numbers and with a variety of spacings and distributions suitable to enable the motor to operate. For example, a motor may typically comprise between about $10^1$ and $10^4$ actuators of each type, and the spacings between actuators of the same type may be between about $10^{-9}$ and $10^{-7}$ metres. Because each step of a described motor device can be effected by actuation of molecules, the devices can be used to provide very small step sizes, for example in the range of about $10^{-9}$ to $10^{-7}$ metres.

Although certain particular embodiments have been described herein, the skilled person will appreciate that various modifications and changes can be made to these without departing from the scope of the invention as defined by the claims. For example, although some particular geometries and motions of the motors and their application have been described, a wide range of other geometries and motions familiar from macroscale stepper motors may be used in the invention. A single system may employ large numbers of motors according to the invention, with those motors falling into a number of distinct groups each driven by a different combination of signals although all are illuminated by the same light sources. For example, the number of motors per set of light sources could be described in terms of micromoles, such that each light source may drive large numbers of separate motor devices that serve, for example as components of a large number of printer systems.

The invention claimed is:

1. A motor comprising:
   first and second bodies in confrontation with each other; and
   at least a first array and a second array of different corresponding types of optically switchable molecular actuator, each array being fixed on one of the first and second bodies,
   for each type of molecular actuator, the molecular actuators of that type being optically switchable together between at least two different molecular states so as to change their state of interaction with the other of the bodies,
   the molecular actuators of each type being optically switchable substantially independently from each other such that repeated sequential optical switching of both the first and second arrays provides a motor action to drive progressive movement of the first and second bodies relative to each other.

2. The motor of claim 1 wherein the repeated optical switching comprises repeating an ordered switching of each of the types of optical switchable molecular actuator in a first order.

3. The motor of claim 2 arranged such that repeating the ordered switching in the first order drives said progressive movement in a first direction, and repeating the ordered switching in one or more other orders different to the first order drives said progressive movement in one or more other directions different to said first direction.

4. The motor of claim 3 wherein the one or more other orders comprise a second order which is the reverse of the first order.

5. The motor of claim 3 wherein the one or more other directions comprises a second direction which is the opposite of the first direction.

6. The motor of claim 2 wherein the first order comprises at least three time intervals in each of which a different combination of none, one or more of the different types of molecular actuator are activated.

7. The motor of claim 6 wherein the first order comprises at least one time interval in which one of the types of molecular actuator is optically activated and the other is not optically activated.

8. The motor of claim 1 wherein at least two of the arrays are fixed on the same body as each other.

9. The motor of claim 1 wherein at least two of the arrays are interleaved with each other.

10. The motor of claim 1 wherein one or more of the arrays are regular arrays.

11. The motor of claim 1 wherein the states of interaction give rise to a series of stepper positions in the movement of the first and second bodies relative to each other, such that the progressive movement in a particular direction comprises repeated movement to subsequent stepper positions in that direction.

12. The motor of claim 11 further comprising one or more arrays of passive features each array being disposed on one of the bodies, each such array of passive features being arranged to engage with at least one of the arrays of optically switchable molecular actuators disposed on the other of the bodies to thereby define the series of stepper positions.

13. The motor of claim 12 wherein one or more of the arrays of passive features comprises an array of passive molecular elements which are not optically switched when any of the molecular actuators are switched.

14. The motor of claim 12 wherein at least one of the arrays of molecular actuators is arranged to change its state of engagement with at least one of the arrays of passive features when the said array of molecular actuators is optically switched.

15. The motor of claim 12 wherein the motor comprises one or more of: at least three arrays of molecular actuators of different types; and at least two arrays of molecular actuators of different types and one array of passive elements.

16. The motor of claim 1 wherein each molecular actuator of each of one or more of said different types of molecular actuator comprises a molecule from the class of azobenzene molecules.

17. The motor of claim 16 wherein each different type of molecular actuator comprising a molecule from the class of azobenzene molecules comprises a different type of azobenzene molecule or moiety.

18. The motor of claim 1 wherein each molecular actuator of each of one or more of said different types of molecular actuator comprises or is coupled to one or more light-harvesting molecules or moieties.

19. The motor of claim 18 wherein the light-harvesting molecules or one or more of said different types of molecular actuator comprises a boron-dipyrromethene molecule.

20. The motor of claim 1 wherein each of one or more of the different types of molecular actuator is switchable using a different spectrum of light.

21. The motor of claim 1 wherein each of one or more of the different types of molecular actuator is switchable using a different envelope over time of intensity of light.

22. The motor of claim 1 wherein being optically switchable between at least two different molecular states comprises being optically switchable between at least two different molecular conformations.

23. The motor of claim 1 wherein being optically switchable between at least two different molecular states comprises being optically switchable between at least two different states of charge distribution.

24. The motor of claim 1 wherein each molecular actuator of each of one or more of said different types of molecular actuator is in communication with at least two light harvesting molecules.

25. The motor of claim 1 further comprising one or more light sources arranged to selectively optically switch the molecular actuators of each type.

26. The motor of claim 1 further comprising a controller arranged to control the one or more light sources so as to drive progressive movement of the first and second bodies relative to each other.

27. A plurality of motors according to claim 1, wherein each motor comprises a plurality of said types of optically switchable molecular actuators, each motor comprising at least one said type of molecular actuator in common with at least one other of the motors, each motor being drivable by a different combination of optical signals to each of the other molecular actuators.

28. The plurality of motors of claim 27 wherein the motors are arranged such that they all receive the same optical signals as each other.

29. The plurality of motors of claim 27 wherein each motor is arranged to provide a motor action comprising progressive movement along a different axis to each of the other motors.

30. The plurality of motors of claim 27 coupled to a common mechanical load.

31. A method comprising:
providing first and second bodies in confrontation with each other and
at least two arrays of a different corresponding type of optically switchable molecular actuator, each array being fixed on one of the first and second bodies, and
providing repeated sequential independent optical switching of the molecular actuators of each type to provide progressive movement of the first and second bodies relative to each other.

32. The method of claim 31 wherein independently switching the molecular actuators of each type to provide said progressive movement comprises repeating an ordered switching of each of the types of optical switchable molecular actuator.

33. The method of claim 32 comprising reversing the order of the ordered switching to provide progressive movement in a reverse direction.

34. The method of claim 31 wherein the repeated switching order comprises at least three time intervals in each of which a different combination of none, one, or more than one of the different types of molecular actuator are activated.

35. The method of claim 31 wherein one or more of the types of molecular actuators comprises an azobenzene molecule or moiety.

36. The method of claim 31 wherein each molecular actuator is switchable using a different optical signal, the different optical signals comprising one or more of: different frequency spectra; and different intensity profiles over time.

37. A method comprising:
disposing at least first and second arrays of different corresponding types of optically switchable molecular actuators between opposing bodies; and
supplying a repeated sequence of optical signals which switch the molecular actuators so as to provide a progressive motor action between the bodies.

38. The method of claim 37 wherein the arrays of optically switchable molecular actuators are disposed between the opposing bodies in a configuration such that each repeated sequence urges the opposing bodies into at least three different alignments, each alignment corresponding to a different combination of none, one or more of said optical signals.

39. A method of operating a nanoscale stepper motor comprising using at least two different molecules, each of which is switchable between at least two different states by a corresponding control signal, as molecular actuators in the nanoscale stepper motor.

40. The method according to claim 39 wherein each of the one or more different molecules are optically switchable between at least two different states.

41. The method according to claim 39 wherein the molecules comprise one or more of: azobenzenes, aromatically linked pyridines, diarylethenes, dithienylethenes, stilbenes, spiropyrans, fulgides, and phenoxynaphthacene quinones.

42. The method according to claim 39 wherein one or more of the molecules are in communication with a light harvesting molecule coupling the corresponding control signal to the molecule.

* * * * *